(12) United States Patent
Nieuwenhuizen

(10) Patent No.: US 8,703,172 B2
(45) Date of Patent: Apr. 22, 2014

(54) SPHINGOLIPIDS FOR IMPROVEMENT OF THE COMPOSITION OF THE INTESTINAL FLORA

(75) Inventor: Willem Ferdinand Nieuwenhuizen, Bunnik (NL)

(73) Assignee: Nederlandse Organizatie voor Toegepastnatuurwetenschappelijk Onderzoek TNO, Delft (NL)

( * ) Notice: Subject to any disclaimer, the term of this patent is extended or adjusted under 35 U.S.C. 154(b) by 1676 days.

(21) Appl. No.: 10/542,838

(22) PCT Filed: Jan. 20, 2004

(86) PCT No.: PCT/NL2004/000046
§ 371 (c)(1),
(2), (4) Date: Jul. 20, 2005

(87) PCT Pub. No.: WO2004/064819
PCT Pub. Date: Aug. 5, 2004

(65) Prior Publication Data
US 2006/0134182 A1   Jun. 22, 2006

(30) Foreign Application Priority Data
Jan. 20, 2003 (NL) ...................................... 1022443

(51) Int. Cl.
*A61K 47/00* (2006.01)
(52) U.S. Cl.
USPC ........................................................ 424/439
(58) Field of Classification Search
None
See application file for complete search history.

(56) References Cited

U.S. PATENT DOCUMENTS

| | | | |
|---|---|---|---|
| 3,622,666 A * | 11/1971 | Cook et al. ...................... | 514/25 |
| 5,190,876 A | 3/1993 | Kinkade, Jr. et al. | |
| 5,232,837 A | 8/1993 | Merrill, Jr. et al. | |
| 5,374,616 A | 12/1994 | Spiegel et al. | |
| 5,478,860 A | 12/1995 | Wheeler et al. | |
| 5,519,007 A | 5/1996 | Della Valle et al. | |
| 5,830,853 A | 11/1998 | Baeckstroem et al. | |
| 6,147,118 A | 11/2000 | Lambers et al. | |
| 6,239,297 B1 * | 5/2001 | Takesako et al. ............... | 554/58 |
| 6,562,606 B1 | 5/2003 | Elias et al. | |
| 6,610,835 B1 * | 8/2003 | Liotta et al. .................... | 536/4.1 |

(Continued)

FOREIGN PATENT DOCUMENTS

| | | |
|---|---|---|
| DE | 196 02 108 | 7/1997 |
| EP | 0 373 038 | 6/1990 |

(Continued)

OTHER PUBLICATIONS

Machine translation of JP 2003-252765 (Jan. 2011).*

(Continued)

*Primary Examiner* — Paul Dickinson
(74) *Attorney, Agent, or Firm* — Preti Flaherty Beliveau & Pachios LLP

(57) ABSTRACT

The present invention relates to a method for improving the composition of the intestinal flora, to a food comprising a sphingolipid for use in such a method, to methods for the preparation of such a food and to the use of sphingolipids for the preparation of a medicine for improving the composition of the intestinal flora. More in particular, the present invention relates to a method and food in which a sphingolipid chosen from the group consisting of phytosphingosine, sphingosine, lysosphingomyelin and sphinganine, or a precursor, a derivative, or suitable salt thereof is used.

7 Claims, 4 Drawing Sheets

(56) References Cited

U.S. PATENT DOCUMENTS

| | | |
|---|---|---|
| 2001/0011076 A1 | 8/2001 | Schwartz et al. |
| 2002/0110587 A1 | 8/2002 | Hope et al. |
| 2002/0182250 A1 | 12/2002 | Hori et al. |
| 2003/0049286 A1 | 3/2003 | Granger et al. |
| 2003/0109044 A1 | 6/2003 | Logan et al. |
| 2004/0047851 A1 | 3/2004 | Tabas et al. |
| 2004/0063667 A1 | 4/2004 | Kishikawa et al. |
| 2004/0147615 A1 | 7/2004 | Rinehart et al. |
| 2004/0171557 A1 | 9/2004 | Iian et al. |
| 2007/0098808 A1 | 5/2007 | Sampalis |

FOREIGN PATENT DOCUMENTS

| | | |
|---|---|---|
| EP | 0 988 860 | 3/2000 |
| EP | 1 291 340 | 3/2003 |
| EP | 1 452 181 | 9/2004 |
| FR | 2 492 259 A | 4/1982 |
| FR | 2 820 037 A | 8/2002 |
| JP | 61 152632 | 7/1986 |
| JP | 5-320048 | 12/1993 |
| JP | 63 044842 A | 2/1998 |
| JP | 11 269074 | 10/1999 |
| JP | 2000/350563 | 12/2000 |
| JP | 2001/158735 | 6/2001 |
| JP | 2001/158736 | 6/2001 |
| JP | 2001 213858 A | 8/2001 |
| JP | 2002/068998 | 3/2002 |
| JP | 2002/226394 | 8/2002 |
| JP | 2003 137894 | 5/2003 |
| JP | 2003-252765 | 9/2003 |
| KR | 2001 008 569 A | 2/2001 |
| WO | WO 92/03129 | 3/1992 |
| WO | WO 95/32002 | 11/1995 |
| WO | WO 97/11706 A | 4/1997 |
| WO | WO 9726891 A1 * | 7/1997 |
| WO | WO 97/36996 | 10/1997 |
| WO | WO 99/41266 A | 8/1999 |
| WO | WO 99/61581 | 12/1999 |
| WO | WO 00/50574 | 8/2000 |
| WO | WO 01/60807 | 8/2001 |
| WO | WO 01/72701 | 10/2001 |
| WO | WO 02/34062 | 5/2002 |
| WO | WO 0234062 A1 * | 5/2002 |
| WO | WO 02/102394 | 12/2002 |
| WO | WO 03/011873 | 2/2003 |
| WO | WO 03/088761 | 10/2003 |
| WO | WO 03/096983 | 11/2003 |
| WO | WO 2004/016257 | 2/2004 |
| WO | WO 2004/064819 | 8/2004 |
| WO | WO 2004/064820 | 8/2004 |
| WO | WO 2004/064823 | 8/2004 |
| WO | WO 2004/096140 | 11/2004 |

OTHER PUBLICATIONS

Machine translation of WO 9726891 A1, Feb. 2012.*

Vesper, H. et al.: "Sphingolipids in Food and the Emerging Importance of Sphingolipids to Nutrition" Journal of Nutrition, vol. 129, 1999, pp. 1239-1250.

Fantini, J. et al.: "Synthetic Soluble Analogs of Galactosylceramide (GalCer) Bind to the V3 Domain of HIV-1 gp120 and Inhibit HIV-1-induced Fusion and Entry" Journal of Biological Chemistry, vol. 272, No. 11, 1997, pp. 7245-7252.

Rueda, R. et al.: "Addition of gangliosides to an adapted milk formula modifies levels of fecal Escherichia coli in preterm newborn infants" J. Pediatr., vol. 133, 1998, pp. 90-94.

Merrill Jr., A. H. et al.: "Role of dietary sphingolipids and inhibitors of sphingolipid metabolism in cancer and other diseases" Journal of Nutrition 1995 United States, vol. 125, No. 6 Suppl., 1995, pp. 1677S-1682S.

Bibel, D. J. et al.: "Antimicrobial Activity of Sphingosines" Journal of Investigative Dermatology, vol. 98, No. 3, 1992, pp. 269-273.

Chung, N. et al.: "Phytosphingosine as a specific inhibitor of growth and nutrient import in Saccharomyces cerevisiae." The Journal of Biological Chemistry. United States Sep. 21, 2001, vol. 276, No. 38, Sep. 21, 2001, pp. 35614-35621.

Soucek, Z. et al., "Gastrointestinal Bacteria of Certain Antarctic Birds and Mammals," Applied Microbiology, vol. 20, No. 4, Oct. 1970, p. 561-566, American Society for Microbiology.

Ley, R. et al., "Evolution of Mammals and Their Gut Microbes," www.sciencemag.org, Science, vol. 320, Jun. 20, 2008, p. 1647-1650.

Pang, X. et al., "Inter-species transplantation of gut microbiota from human to pigs," The ISME Journal (2007) 1, p. 156-162.

Sprong, R. Corinne et al., "Bactericidal Activities of Milk Lipids," Antimicrobial Agents and Chemotherapy, vol. 45, No. 4, Apr. 2001, p. 1298-1301, American Society for Microbiology.

Sprong, C. et al., "Phospholipid-Rich Butter Milk Decreases the Gastro-Intestinal Survival and Translocation of Listeria in Rats," A1090 AGA Abstracts, Gastroenterology, vol. 114, No. 4.

Sprong, R.C. et al., "Bovine milk fat components inhibit food-borne pathogens," International Dairy Journal 12 (2002) p. 209-215, Elsevier Science Ltd., 1998.

Schmelz, E. et al., "Uptake and Metabolism of Sphingolipids in Isolated Intestinal Loops of Mice," The Journal of Nutrition, 1994, American Institute of Nutrition, p. 702-712.

Jensen, R., "Composition of Bovine Milk Lipids," Journal of the American Oil Chemists' Society, vol. 50, Jun. 1973, p. 186-192.

Astaire, J. C. et al., "Concentration of Polar MFGM Lipids from Buttermilk by Microfiltration and Supercritical Fluid Extraction," Journal of Dairy Science, vol. 86, No. 7, 2003, p. 2297-2307.

Auge, Nathalie et al.: "Sphingomyelin metabolites in vascular cell signaling and atherogensis" Progress in Lipid Research, vol. 39, No. 3, May 2000, pp. 207-229.

Beers, M.H. and R. Berkow: "The Merck Manual of Diagnosis and Therapy, seventeenth edition" 1999, Merck Research Laboratories, Whitehouse Station, N.J., XP002311213 p. 1655, col. 1, paragraph 4-p. 1656, col. 1, paragraph 3.

Beers, M.H. and R. Berkow: "The Merck Manual of Diagnosis and Therapy, seventeenth edition" 1999, Merck Research Laboratories, Whitehouse Station, N.J., XP002341450 p. 1062; tables 148-4.

Bischoff, A. et al..: "Sphingosine-1-Phosphate and sphingosylphosphorylcholine constrict renal and mesenteric microvessels in vitro" British Journal of Pharmacology, Basingstoke, Hants, GB, vol. 130, No. 8, Aug. 2000, pp. 1871-1877.

Chatterjee, Subroto: "Sphingolipids in atherosclerosis and vascular biology" Arteriosclerosis Thrombosis and Vascular Biology, vol. 18, No. 10, Oct. 1998, pp. 1523-1533.

Chong, P.H. et al.: "Atorvastatin calcium: an addition to HMG-CoA reductase inhibitors." Pharmacotherapy, vol. 17(6), pp. 1157-1177; 1997.

Davaille et al. 2000. J. Biol. Chem., vol. 275, No. 44, pp. 34628-34633.

Howell et al. 2002. Current Organic Chemistry, vol. 6, No. 4, 2002, pp. 365-391.

Jiang, Xian-Cheng et al.: "Plasma sphingomyelin level as a risk factor for coronary artery disease" Arteriosclerosis Thrombosis and Vascular Biology, vol. 20, No. 12, Dec. 2000, pp. 2614-2618.

Jung et al. 1996. Journal of Natural Products, vol. 59, No. 3, pp. 319-322.

Kim, et al. 2000. Phytotherapy Res., 14(6), 448-451.

Leventhal, A. R. et al.: "Acid sphingomyelinase-deficient macrophages have defective cholesterol trafficking and efflux." The Journal of Biological Chemistry. Nov. 30, 2001, vol. 276, No. 48, Nov. 30, 2001, pp. 44976-44983.

Mei Jie et al.: "$C_2$-CEramide influences the expression and insulin-mediated regulation of cyclic nucleotide phosphodiesterase 3B and lipolysis in 3T3-I1 adipocytes." Diabetes, vol. 51(3), pp. 631-637; 2002.

Ortenberg et al: Farmakologiya i Toksikologiya (Moscow), vol. 47, No. 4, 1984, pp. 102-105.

(56) References Cited

OTHER PUBLICATIONS

Schmelz, E. M. et al.: "Sphingomyelin consumption suppresses aberrant colonic crypt foci and increases the proportion of adenomas versus adenocarcinomas in cf1 mice treated with 1,2-dimethylhydrazine: implications for dietary sphingolipids and colon carcinogenesis" Cancer Research, American Association for Cancer Research, Baltimore, MD, US, vol. 56, No. 21, Nov. 1, 1996, pp. 4936-4941.

Sosnowski et al. 1997. Journal of Urology, vol. 158, No. 1, pp. 269-274.

Sprong, R.C. et al.: "Bovine milk fat components inhibit food-borne pathogens." International Dairy Journal, vol. 12, pp. 209-215, 2002.

Thurman et al. 1994. Transplant Int.: Off. J. Eur. Soc. For Organ Transplantation. 1994, vol. 7 suppl 1, 1994, pp. s167-s170.

Turinsky J et al: "Effect of sphingoid bases on basal and insulin-induced glucose uptake by skeletal muscle", Journal of Cell Biology, vol. 115, No. 3 Part 2, 1991, p. 222A; & abstracts of papers presented at the thirty-first annual meeting of the american society for cell bi.

Van Veldhoven Paul P et al: "Do sphingoid bases interact with the peroxisome proliferator activated receptor alpha (PPAR-alpha)?"; Cellular Signaling, vol. 12, No. 7, Jul. 2000, pp. 475-479, p. 477, col. 2, lines 13-29.

Viola, G. et al.: "Absorption and distribution of arachidonate in rats receiving lysophospholipids by oral route" Journal of Lipid Research, Bethesda, MD, US, vol. 34, No. 11, 1993, pp. 1843-1852.

Yamada, T. et al.: "Growth inhibition of pancreatic cancer cells by sphingosylphosphorylcholine and influence of culture conditions" CMLS, Cell. mol. life. sci. vol. 53, pp. 435-441, 1997.

Zheng et al. 2002. Hepatology, vol. 36, No. 4 part 2, p. 215a. Abstract No. 196.

\* cited by examiner

SPHINGOLIPIDS FOR IMPROVEMENT OF THE COMPOSITION OF THE INTESTINAL FLORA

This application is a §371 national phase filing of PCT/NL2004/000046 filed Jan. 20, 2004; and claims priority to a Dutch application NL 1022443 filed Jan. 20, 2003.

FIELD OF THE INVENTION

The invention relates to a method for improving the composition of the intestinal flora, to the use of sphingolipids for improving the composition of the intestinal flora, to a pharmaceutical preparation and a food comprising a sphingolipid for improving the composition of the intestinal flora and to methods for the preparation thereof.

BACKGROUND OF THE INVENTION

Humans and animals regularly fall ill due to microbial infections or due to a disturbance of their intestinal flora by a, usually foreign, microorganism. In the treatment of such infections, usually, antibiotics are used to remove the undesired pathogenic organisms.

A drawback of the use of antibiotics is that not only the pathogenic microorganisms, but also the useful and essential microorganisms in the intestinal flora are killed by the antibiotics. The patient is severely troubled by this, inter alia by the occurrence of diarrhea, and a period of recovery from the intestinal disturbance is necessary. There are only few antibiotics that have such a selective activity against undesired microorganisms that they can prevent the occurrence of intestinal disturbances when using antibiotics.

Another drawback of the use of antibiotics is that certain individuals exhibit allergic reactions to certain antibiotics, such as penicillin. The consequence of this is that those persons are preferably not treated with such an antibiotic and that they should avoid contact with such an antibiotic as much as possible.

Currently, antibiotics are often used in animal feed to reduce the metabolism of the intestinal flora and to improve the availability of nutrients for the host. In this manner, the meat yield can be increased. Further, antibiotics are used to control infections. However, meat from cattle treated with antibiotic is, for various reasons, not considered suitable for human consumption. Also, the milk of dairy cattle treated with antibiotic is unsuitable for human consumption. Thus, the use of antibiotics in cattle feed is under dispute and there are hardly any alternatives yet.

SUMMARY OF THE INVENTION

It has now surprisingly been found that a number of types of sphingolipids can selectively kill certain undesired bacteria in the intestine while other bacterial species are left virtually undisturbed. For instance, *Clostridium difficile*, a common pathogenic bacterium which causes diarrhea and is difficult to control by means of antibiotics, is very effectively killed by certain sphingolipids while other important and useful bacteria in the intestinal flora are left undisturbed.

The sphingolipids which have this activity can therefore very suitably be used in a method for the improvement of the composition of the intestinal flora in that certain, undesired bacteria can be killed off by means of the method while other bacterial species, which are important for the functioning of the intestinal flora, can be left virtually undisturbed or are much less inhibited in their growth by means of the method.

Therefore, in a first aspect, the present invention relates to a method for improving the composition of the intestinal flora of a bird or a mammal, including a human, comprising administering, to this bird or mammal, a food in which one or more sphingolipids chosen from the group consisting of phytosphingosine, sphingosine, lysosphingomyelin and sphinganine or a precursor, a derivative, or suitable salt thereof are overabundant.

In a second aspect, the present invention relates to a food in which one or more sphingolipids chosen from the group consisting of phytosphingosine, sphingosine, lysosphingomyelin and sphinganine or a precursor, a derivative, or suitable salt thereof are overabundant.

Such a food may very suitably be an animal feed and thus forms an important alternative for antibiotics to improve the growth of, for instance, breeding cattle. Therefore, on the basis of this invention, sphingolipids form an alternative for the use of antibiotics in cattle feed. In a preferred embodiment, such a food comprises the sphingolipid phytosphingosine.

Other aspects of the present invention will become clear in the description below.

DETAILED DESCRIPTION OF THE INVENTION

Figure 1A:
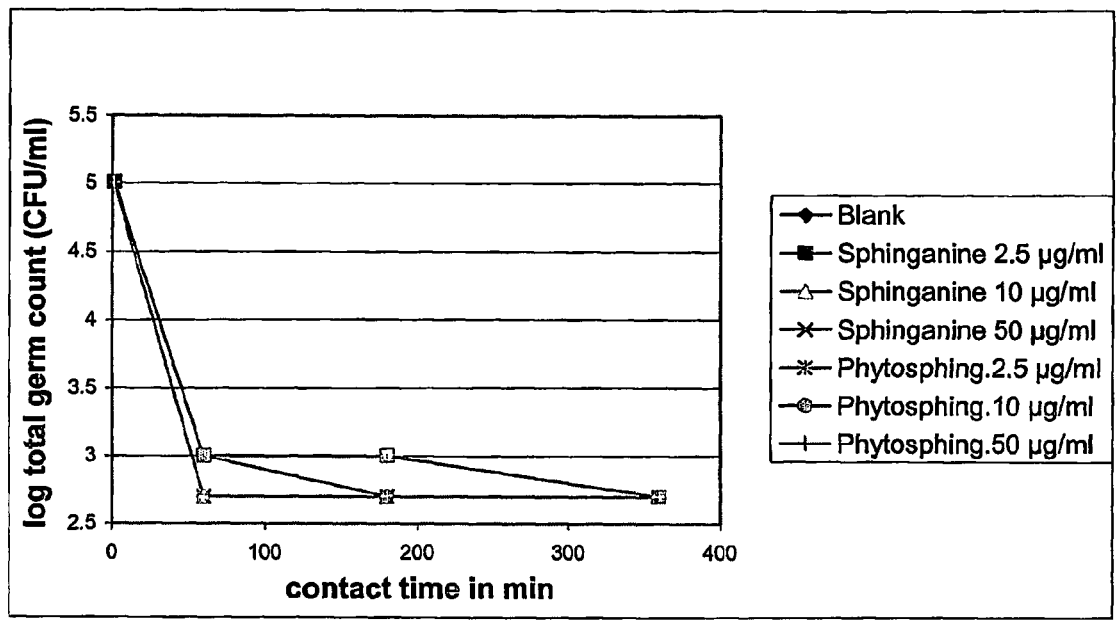
FIG. 1 shows the concentration and time-dependent antimicrobial activity of sphinganine and phytosphingosine against *Lactobacillus acidophilus* with (A) and without (B) bile and against *Clostridium difficile* with (C) and without (D) bile as described in Example 1.
Figure 1B:
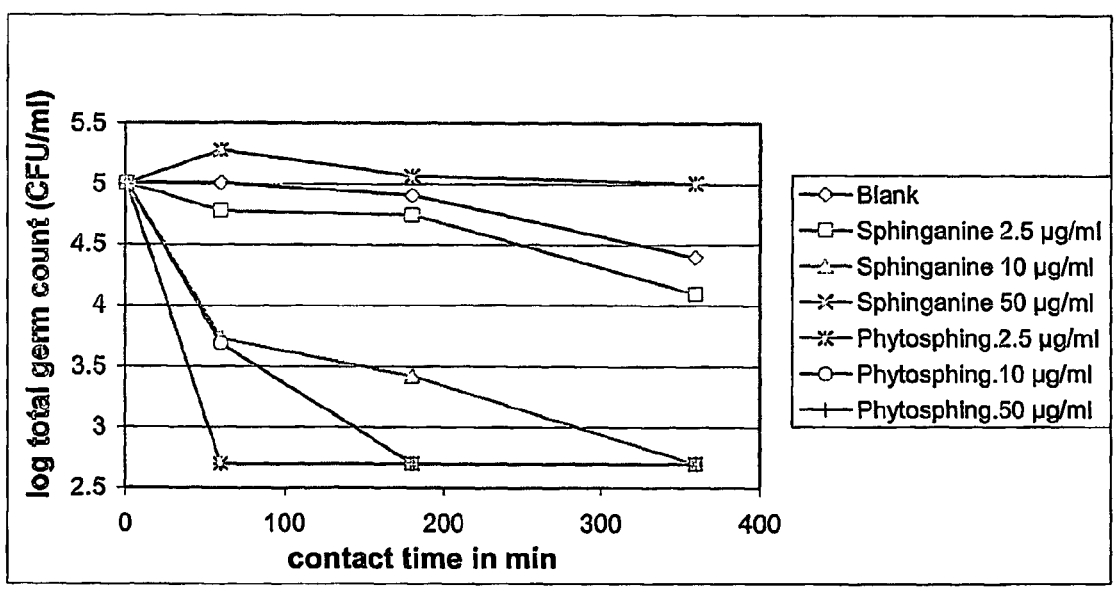
Figure 1C:
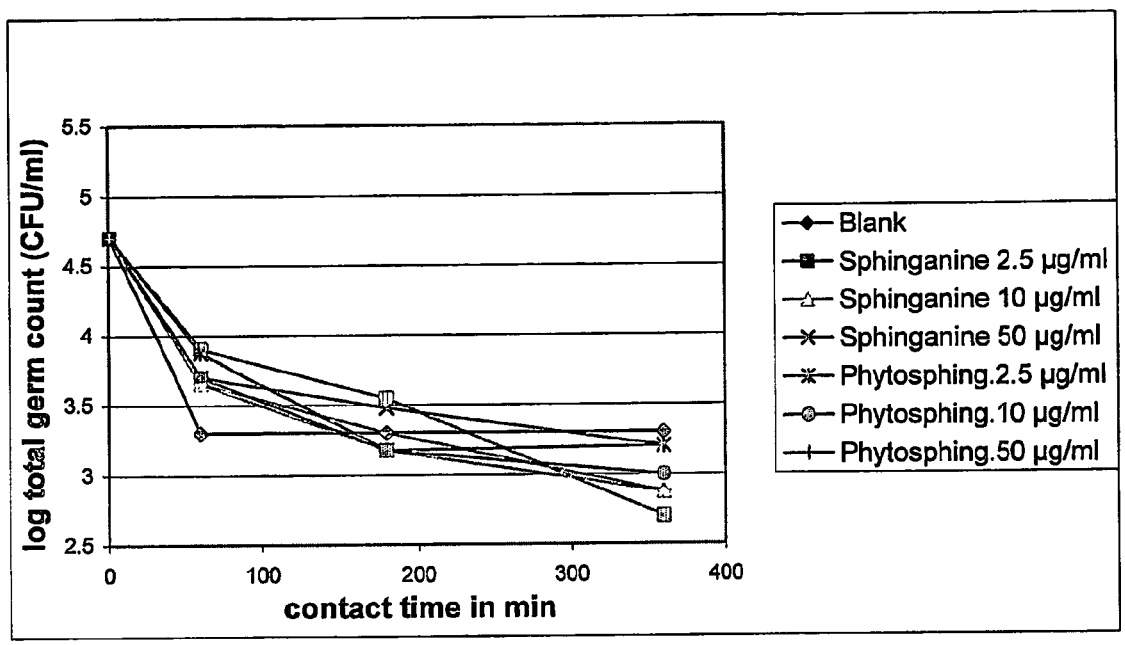
Figure 1D:
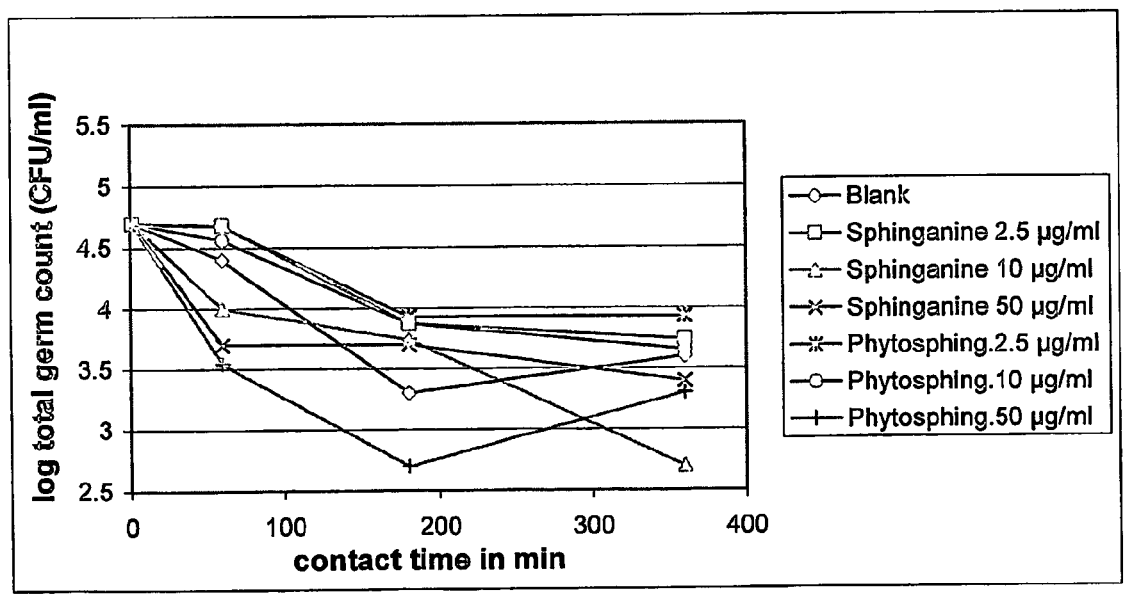

Sphingolipids are small lipids which occur in low concentrations in food and they form a small but important constituent of the cells of plants, animals and humans. Because sphingolipids occur naturally in humans and animals, an advantage of the use of sphingolipids in humans is that individuals with an antibiotic allergy or a 'chemophobia' can be offered an important alternative for the existing (chemical) antibiotics.

Sphingolipids are generally built up from a long sphingoid base (sphingosine, sphinganine, 4-hydroxysphinganine, or a related compound) as the central group of the molecule or "backbone" (see inter alia Karlsson. 1970. Chem. Phys. Lipids, 5:6-43), which is usually modified with an amide-linked long-chain fatty acid and a head group. Approximately 300 classes of sphingolipids are known, with different head groups (choline phosphate, glucose, galactose, polysaccharides) and with different fatty acids and sphingoid bases (see inter alia Merrill & Sweeley. 1996. New Comprehensive Biochemistry: Biochemistry of Lipids, Lipoproteins, and Membranes, (Vance, D. E. & Vance, J. E., eds.), pp. 309-338, Elsevier Science, Amsterdam).

The simplest sphingolipids such as sphingosine and sphinganine are normally found in food only in very low concentrations. The richest sphingolipid sources are dairy products, eggs and soybeans. The most important sphingolipids in our food are sphingomyelin (milk and eggs) and ceramide (meat). Fat milk mainly contains sphingomyelin, but also contains glucosylceramide and lactosylceramide. Potato, apple, tomato, spinach, paprika and rice mainly contain cerebrosides in low concentrations.

As far as known, sphingolipids form a non-essential constituent of our food; the bodies of humans and animals are able to synthesize sphingolipids. The sphingolipids which arrive in the gastrointestinal tract together with the food are hydrolyzed to inter alia sphingosine and ceramides, partly by the intestinal flora itself and partly by hydrolytic enzymes present in the gastrointestinal tract, such as alkaline and neutral sphingomyelinases and ceramidases. There are indications that the hydrolysis products ceramide and sphingosine play a key role in cell growth, cell differentiation, apoptosis and other important physiological processes. Despite the presence of these hydrolytic systems, in rats, still approximately 25% of the sphingomyelin fed is found in the feces (see inter alia Nilsson. 1968. Biochim. Biophy. Acta. 164: 575-584 and Nilsson. 1969. Biochim. Biophys. Acta 187: 113-121).

Sphingosine and sphingosine analogs are known to be able to inhibit the growth and metastasis of human and animal tumor cells (see for instance EP 0 381 514). It is also known that addition of sphingomyelin to the feed of rats can considerably reduce the chance of malignant, chemically induced intestinal cancer.

Sphingolipids are also used in pharmaceutical compositions for the protection of skin and/or hair against the harmful effects of air pollution (see for instance U.S. Pat. No. 5,869,034).

The antimicrobial activity of sphingosine as a constituent of the epidermis of the skin against bacteria such as *Staphylococcus aureus, Candida albicans* and *Propionibacterium acnes* is known, inter alia from dermatology (Bibel et al. 1992. J. Invest. Dermatol. 98(3):269-73; Bibel et al. 1995. Clin Exp Dermatol 20(5):395-400). The use of topical ointments for controlling skin infections is described therein.

However, it has now surprisingly been found that certain sphingolipids have a selective killing activity against microorganisms, and that this selective killing activity is also observed in the large intestine, so that a method is thus provided by which the composition of the intestinal flora can be modified and improved.

In the present invention, the composition of the intestinal flora of a bird or a mammal is understood to mean the group structure of the community of microorganisms present in the gastrointestinal tract of this bird or of this mammal and which characteristically comprises different groups of microorganisms, which group structure is in a substantially stable condition in a substantially stable environmental condition and is characteristic of a certain bird or of a certain mammal.

Herein, a group of microorganisms is understood to mean a group of microorganisms which can be distinguished from another group on the basis of one or more specific genotypic or phenotypic characteristics. Such a group may comprise a taxonomic group such as a phylum, a family, a genus, a species or a strain, but also a group which is methodologically classified such as a phylogenetic cluster, a ribotype, an isolate, a serotype, or a morphotype.

In the determination of a composition of a microbial population, the ratio in which the different groups are found in the population may be. determined, but also the proportion of a group in the population. A ratio or proportion may, for instance, be expressed in a cell number, but also in a weight of a cell or a cell component, such as a weight of a nucleic acid, or a fluorescence intensity. A skilled person will understand that the manner in which a composition of a microbial population is expressed depends on the method by which this composition is determined.

Herein, an improvement of the intestinal flora is defined as a change of the composition of the intestinal flora of a bird or a mammal, whereby the proportion in the population of harmful bacteria is reduced, or as stabilization of the intestinal flora in a condition in which it is in balance. It is known to a skilled person which bacteria are generally identified as being healthy to the intestinal flora (e.g. *Lactobacillus* and *Bifidobacterium* spp.) and which bacteria are generally identified as being harmful to the intestinal flora (e.g. *Clostridiuin difficile*). For instance, harmful bacteria are associated with the development of diarrhea, infections of the gastrointestinal tract, liver damage and/or intestinal cancer, while healthy or useful bacteria are associated with inhibiting the growth of harmful bacteria, stimulating immunological functions, reducing problems resulting from distension due to gas, improving the digestion and absorption of nutrients and synthesizing vitamins.

The present invention provides a method for improving the composition of the intestinal flora of a bird or a mammal. This method comprises administering, to this bird or to this mammal, including humans, a pharmaceutical preparation or a food comprising a sphingolipid or a precursor, a derivative, or suitable salt thereof, which sphingolipid is chosen from the group consisting of phytosphingosine, sphingosine, lysosphingomyelin and sphinganine, and in which food, this sphingolipid is overabundant.

The term "overabundant" or "overabundance" relates to a content of a constituent in a composition which is higher than would naturally or normally or without human intervention be present in such a composition or would be found therein. The overabundance of a constituent can be the result of the specific addition of a constituent to a composition which does not normally comprise this constituent, i.e. by an enrichment of this composition with this constituent. Overabundance of a constituent may also be the result of the specific addition of a constituent to a composition which normally already comprises this constituent, but whose concentration or content is increased by the addition to values which are normally not present in such a composition; this also involves enrichment of the composition with the constituent.

Because contents of sphingolipids such as phytosphingosine, sphingosine, lysosphingomyelin or sphinganine greatly differ in different foods, there is no one general value for the content which will involve overabundance of, or enrichment with a certain sphingolipid. In, for instance, milk, which normally contains quite a lot of sphingomyelin, overabundance will occur at a higher content than in, for instance, a potato in which, mainly, cerebrosides are present.

Herein, a "pharmaceutical preparation" is defined as a composition comprising a pharmaceutically active constituent and excipients, which composition has been made suitable for administration to the body of a bird or a mammal and which composition is administered for a specific therapeutic use.

A pharmaceutical preparation according to the present invention is a composition comprising a sphingolipid, chosen from the group consisting of phytosphingosine, sphingosine, lysosphingomyelin and sphinganine, as a pharmaceutically active constituent, and excipients, and which composition may be, preferably orally, administered for the improvement of the composition of the intestinal flora of the bird or the mammal.

Herein, a "food" is defined as a nutritious constituent to be ingested orally which may be ingested independently or in addition to the normal food and which, in the latter form, may also be termed nutritional supplement. However, the composition of a food does not essentially differ from a nutritional supplement.

In the present invention, a "nutritional supplement" is defined as a composition which may be consumed supplementary to the normal food and comprises constituents which are not, to a small extent, or to an insufficient extent found in the normal food and of which sufficient or increased consumption is desired. Preferably, a nutritional supplement is a composition suitable for human consumption which comprises sphingolipids in increased concentrations or in overabundance. A nutritional supplement according to the present invention may further have other properties suitable for human consumption, such as for instance texture, taste and smell, and, for instance, also nutritional value. A nutritional supplement may also be suitable for animal consumption.

With respect to the use of sphingolipids according to embodiments of the present invention, the use of a suitable salt of a sphingolipid is preferred because the salt form strongly influences the solubility and therefore the rapid availability of the compound.

Herein, a "suitable salt" is defined as a salt in which the desired biological activity of the sphingolipid is maintained and has minimal undesired toxicological effects. Non-limiting examples of such a salt are (a) acid addition salts formed with inorganic acids (for instance hydrochloric acid, hydrogen bromide, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmitic acid, polyglutamic acid, naphthalene sulfonic acid, naphthalene disulfonic acid and polygalacturonic acid; (b) base addition salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); for instance a zinc tannate or the like.

Herein, a "derivative" or "analog" is defined as a sphingolipid which has been subjected to chemical modification. Derivatization may comprise the substitution of certain chemical groups to the sphingolipid. Such derivatizations are known from the state of the art. The derivatives and analogs maintain the biological activity of the natural sphingolipid and function in a similar manner, but can offer advantages to the molecule such as a longer life, a resistance to decomposition or an increased activity.

Herein, a "precursor" is defined as a derivative of which, specifically, the resistance against decomposition by, for instance, the digestive tract or other decomposition systems of the body has been increased as a result of, for instance, chemical modification of the molecule. Such a precursor can be converted by the body or in the body, for instance by enzymatic decomposition, to a sphingolipid chosen from the group consisting of phytosphingosine, sphingosine, lysosphingomyelin and sphinganine or a derivative thereof which shows selective antimicrobial activity in the intestine and can thus improve the composition of the intestinal flora.

A known problem associated with the administration of sphingolipids is that they can be metabolized, as described hereinabove, before they reach the location where they can be therapeutically active. This is particularly a problem for the use of sphingolipids in the digestive tract.

This problem can be solved by administering a sphingolipid, or an analog or a physiological derivative thereof, alone or in combination, as a so-called precursor compound comprising certain substituents so that this compound cannot be metabolized or can be metabolized to a lesser extent. The precursors are preferably resistant to hydrolysis in the upper parts of the digestive tract, and are, for instance, separated relatively easily in the cecum and colon, if the active compound is therapeutically active mainly in the cecum and colon. This increases the amount of compound arriving at the location where the active compound is therapeutically active. For instance, a precursor may be used which may be separated in vivo by a suitable enzyme so that an active sphingolipid chosen from the group consisting of phytosphingosine, sphingosine, lysosphingomyelin and sphinganine is released. Such a method is inter alia known from WO 99/41266. A suitable precursor is, for instance, sphingomyelin or a derivative or a suitable salt thereof, which may be converted into sphingosine by, for instance, sphingomyelinase.

The origin of the sphingolipids does not influence their usability for the present invention. For instance, phytosphingosine may be obtained from *Pichia ciferii* (see for instance U.S. Pat. No. 6,204,006). Further, lysosphingomyelin may be obtained from, for instance, eggs after chemical or enzymatic hydrolysis of the N-acyl compound of sphingomyelin. In principle, any origin is suitable and sphingolipids may also be isolated from, for instance, milk, blood, meat, brains or soy for use in a food, nutritional supplement, pharmaceutical preparation or method according to the invention.

Also, sphingolipids and sphingolipid derivatives, or precursors or suitable salts thereof which are synthetically (chemically) prepared may be used in the present invention.

Methods for preparing sphingolipids and sphingolipid derivatives are known from inter alia EP 0 940 409, WO 98/03529 and WO 99/50433 and a skilled person will be able to manufacture derivatives in a known manner and to test these for increased antimicrobial activity, for more selective activity, or for reduced side effects in order to obtain sphingolipid derivatives which may be used in the present invention.

Certain sphingolipids, such as sphingosine, sphinganine and particularly sphingomyelin are already naturally present in foods which are eaten by many mammals. For instance, cow milk contains 100-200 nmol/ml of sphingomyelin (Zeisel et al. 1986. J. Nutr. 116:50-58), that is, approximately 0.01 wt. %. Sphingomyelin is the most common complex sphingolipid in milk, while sphingosine forms the most common free sphingoid base. The total amounts of sphingomyelin and sphingosine in milk are approximately equal. "Nonfat dry milk" contains approx. 0.004 wt % of sphingosine.

In soy, by contrast, the free sphingosine fraction is only approximately 0.2% of the amount of sphingomyelin, which is approximately 500 nmol/g of dry weight, that is, 0.03-0.04 wt. % (Ahn and Schroeder. 2002. J Food Sci 67:522-524). Thus, not every food contains an equal amount of sphingolipid and not every sphingolipid is present in equal amounts in different foods. The amount of sphingosine naturally present in soybean meal (1.3 nmol/g of dry weight, that is, approx. 0.00004 wt. %; Ahn and Schroeder. 2002. J. Food Sci. 67:522-524) is too low to be used in a method according to the present invention.

Thus, in order to use soybean meal as food in a method according to the present invention, of this soybean meal, the content of one or more sphingolipids chosen from the group consisting of phytosphingosine, sphingosine, lysosphingomyelin and sphinganine needs to be increased to a concentration at which, after consumption of this soybean meal by a bird or a mammal, including a human, the intestinal flora is improved by the activity of this sphingolipid, or specific bacteria in this intestinal flora are killed by this or are at least strongly inhibited in their growth by this. For this purpose, one or more of these sphingolipids are to be provided in overabundance in this soybean meal. For this purpose, to soybean meal, a certain amount of this sphingolipid may be added, or, for instance, a genetically modified variant of a soy plant may be bred whose beans produce an increased content of this sphingolipid, after which, from these beans, a soybean meal having an increased content or overabundance of this sphingolipid can be obtained. Many methods are, in principle, suitable to make a sphingolipid overabundant in a food or provide it in overabundance.

It was found that, on agar plates, the growth of the bacteria tested was already inhibited at a concentration of sphingolipid content of 20 ppm. It was further found that the intestinal content of a pig which was fed with 1 wt. % (approx. 10000 ppm) of phytosphingosine in the feed could contain an amount of phytosphingosine of approx. 77 ppm/gram of dry weight at the end of the small intestine. Despite the decomposition of the phytosphingosine in the gastrointestinal tract, it is found that ample phytosphingosine remains for an antimicrobial activity and therefore for an improvement of the composition of the intestinal flora.

The present invention relates to a food in which one ore more sphingolipids chosen from the group consisting of phytosphingosine, sphingosine, lysosphingomyelin and sphinganine, or a precursor, a derivative, or suitable salt thereof are overabundant. In a preferred embodiment, such a food comprises 0.05 to 50 wt. %, preferably 0.1 to 10 wt. %, more preferably 1 to 5 wt. % of a sphingolipid chosen from the group consisting of phytosphingosine, sphingosine, lysosphingomyelin and sphinganine, or derivatives, precursors or suitable salts thereof.

In a food according to the invention, one or more sphingolipids chosen from the group of phytosphingosine, sphingosine, lysosphingomyelin and sphinganine are, in any case, used in an effective amount to have a growth-inhibiting or killing activity against the desired microorganisms in the intestine.

In a preferred embodiment, a food according to the present invention comprises the sphingolipid phytosphingosine.

If a food according to the invention is used as animal feed, the food may, for instance, be prepared in the form of a powder, a granule, a wafer, a mash, a lump, a pulp, a paste, a flake, a cake, a (lick) block, a suspension or a syrup.

For administration to humans, the sphingolipid may very suitably be prepared in the form of a nutritional supplement.

To a food and nutritional supplement comprising a sphingolipid, constituents which improve, for instance, the texture, taste or smell may be added. For instance, a food according to the invention may also comprise sources of protein, carbohydrate and fat, as well as vitamins, minerals, electrolytes, trace elements, and other suitable additions, such that the food may be used in the form of a nutritional supplement with nutritional constituents.

As a source of protein, in principle, any protein suitable for use in food formulations and mixtures thereof may be used in a nutritional supplement according to the invention. Such proteins comprise, for instance, animal protein, such as whey protein, whey protein concentrate, whey powder, egg protein, egg albumin, casein or milk albumin, and vegetable protein, such as soy protein, soybean meal or protein from soymilk. For the choice of the protein source, the biological value of the protein can be an important criterion, with, for instance, caseinate, including calcium caseinate, but also whey, milk albumin, egg albumin and whole egg proteins being among the proteins with the highest biological value, because they contain a high content of essential amino acids.

Suitable carbohydrates for use in a nutritional supplement according to the invention comprise, for instance, simple short-chain carbohydrates such as mono and disaccharides but also polysaccharides, or a combination thereof A sugar may be chosen because of desired organoleptic properties. A complex polysaccharide may, for instance, be suitably used as dietary fiber. In certain embodiments, a food supplement according to the invention may also comprise combinations of complex and simple carbohydrates.

As (additional) fats, in principle, all possible fats and oils suitable for consumption may be used.

Vitamins and minerals may, for instance, be added to the nutritional supplement in accordance with applicable rules of health authorities and may comprise all vitamins and minerals recommended by these bodies, such as vitamins A, B1, B2, B12, folic acid, niacin, panthotenic acid, biotin, C, D, E and K. As minerals, for instance, iron, zinc, iodine, calcium, magnesium, chrome and selenium may be added.

Electrolytes such as sodium, potassium and chlorides, and trace elements and other additions may also be comprised in a nutritional supplement according to the invention and are, if present therein, preferably used in the amounts recommended for these substances. A nutritional supplement according to the invention may further comprise constituents such as texture-improving constituents, colorings, aromatic substances, flavorings, spices, fillers, emulsifiers, stabilizers, preservatives, antioxidants, dietary fibers, and other nutritional supplements such as amino acids, choline, lecithin, fatty acids, etc. The choice for such constituents is a matter of formulation, design and preference. The amounts of such constituents which can be added are known to a skilled person, while the choice may, for instance, be guided by the recommended daily amounts (RDA doses) for children and adults.

Emulsifiers may be added for stability of the final product. Examples of suitable emulsifiers comprise, for instance, lecithin (e.g. from egg or soy) and/or mono and diglycerides. As stabilizers, for instance, carob, guar and carrageen gum may be used.

Preservatives may also be added to prolong the storage life of the product. Preferably, preservatives such as potassium sorbate, sodium sorbate, potassium benzoate, sodium benzoate or calcium disodium EDTA are used.

In addition to the above carbohydrates, the nutritional supplement may comprise natural or synthetic sweeteners such as saccharides, cyclamates, aspartamine, aspartame, acesulfame K and/or sorbitol.

Doses for ingestion of the nutritional supplement may vary in size and are not limited to the values corresponding to the recommended amounts. Herein, the term "nutritional supplement" is not intended to be limited to a specific weight or specific dose of the nutritional supplement.

A composition of a nutritional supplement according to the invention may, in principle, have any form suitable for consumption by humans or animals. A suitable embodiment is a composition in the form of a dry powder which may be suspended, dispersed or emulsified in an aqueous liquid such as water, coffee, tea, broth or fruit juice. For this purpose, such a powder may be provided in a unit dose package.

In an alternative preferred embodiment, the composition is tabletted in the form of a dry powder. For this purpose, a composition for a nutritional supplement according to the invention may very suitably be provided with fillers, such as microcrystalline cellulose (MCC) and mannitol, binding agent, such as hydroxypropyl cellulose (HPC), and lubricants, such as stearic acid or other excipients.

A composition of a nutritional supplement according to the invention may also be provided in a liquid preparation in which the solid constituents are suspended, dispersed or emulsified in an aqueous liquid. Such a composition may be mixed directly into another food or may, for instance, be extruded and be processed to granules or other forms.

In an alternative embodiment, a nutritional supplement may be designed in the form of a solid food, such as a bar, cookie or a roll.

In a pharmaceutical preparation or a nutritional supplement which can be used in a method according to the present invention, one ore more sphingolipids chosen from the group of phytosphingosine, sphingosine, lysosphingomyelin and sphinganine can be used in a pharmaceutically effective amount to have a killing activity against the desired microorganisms and to improve the composition of the intestinal flora.

A pharmaceutically effective amount in a pharmaceutical is the amount in that pharmaceutical which results in an effective concentration of, for instance, active phytosphingosine in the intestine of 10 to 50 ppm.

In a pharmaceutical, or in a food or nutritional supplement, the sphingolipid can very suitably be used as a precursor so that the effective amount of the active form of the sphingolipid which can reach the intestine is increased.

A pharmaceutical preparation which can be used in a method according to the invention may very suitably comprise 0.01 to 99.9 wt. % of a sphingolipid chosen from the group consisting of phytosphingosine, sphingosine, lysosphingomyelin and sphinganine. Preferably, a pharmaceutical composition comprises one or more sphingolipids chosen from the group of phytosphingosine, sphingosine, lysosphingomyelin and sphinganine, or a precursor, a derivative or a (pharmaceutically) suitable salt thereof in an amount of 0.01 to 10 wt. %, more preferably of 0.1 to 1 wt. %, and one or more excipients.

Preferably, a pharmaceutical composition according to the invention is intended for or directed to oral administration. Compositions for oral administration will usually comprise an inert diluent or an edible carrier. The compositions may be packaged in, for instance, gelatin capsules or may be tabletted in the form of tablets. For oral therapeutic administration, the active compound may be administered with excipients and, for instance, used in the form of tablets, pastilles or capsules. Pharmaceutically suitable binding agents and/or adjuvants may also be added as constituents of the composition.

The tablets, pills, pastilles, capsules and the like may comprise any of the following constituents or similar compounds: a filler such as microcrystalline cellulose (MCC) or mannitol; a binding agent such as hydroxypropyl cellulose (HPC), tragacanth gum or gelatin; an excipient such as starch or lactose; a disintegrating agent such as alginate or corn starch; a lubricant such as magnesium stearate, a sweetener such as sucrose or saccharose; or a flavoring such as peppermint or methyl salicylic acid. When a dosage form in the form of a capsule is used, it may comprise, in addition to the above constituents, a liquid carrier such as oil. Further, the dosage forms may be designed with, for instance, coating layers from sugar, shellac or other agents. The constituents of the pharmaceutical composition are preferably chosen such that they do not reduce the desired activity of the sphingolipid.

For an oral pharmaceutical, one or more sphingolipids or derivatives or (pharmaceutically) suitable salts thereof may also be administered in the form of, for instance, an elixir, a suspension, a syrup, a wafer or a chewing gum.

In a third aspect, the present invention relates to the use of a sphingolipid chosen from the group consisting of phytosphingosine, sphingosine, lysosphingomyelin and sphinganine, for the preparation of a medicine for the improvement of the composition of the intestinal flora.

This aspect of the invention has its basis in the selective character of the bactericidal activity of the sphingolipids according to the invention in the intestine. The selective killing of certain types of microorganisms makes a sphingolipid, used according to this aspect of the invention, eminently suitable to improve the intestinal flora.

In the present invention, improving the intestinal flora is understood to mean the selective killing or inhibiting of microorganisms in the intestine which are harmful or undesired or non-essential to intestinal health, such that the microorganisms which are useful, desired and essential for a proper functioning of the intestinal flora are not affected, and where, due to the killing of these microorganisms, the (species) composition of the intestinal flora is modified in a desired direction. In addition to a bactericidal activity of the sphingolipid, in the present invention, also, a bacteriostatic activity of the sphingolipid is provided.

Thus, by using a sphingolipid according to the invention, the presence of *C. difficile* can be controlled, while the presence of *Lactobacillus* species, which are generally identified as useful organisms in the intestine, is not affected.

Further, the presence of, for instance, certain Gram-positive bacterial species in the intestinal flora can be reduced by use of a pharmaceutical composition or a food or nutritional supplement according to the invention. This allows the promotion of the growth of certain animals without antibiotics needing to be used:

In a fourth aspect, the present invention relates to a method for preparing a food or nutritional supplement according to the invention, comprising incorporating a sphingolipid chosen from the group consisting of phytosphingosine, sphingosine, lysosphingomyelin and sphinganine, or a precursor or a derivative thereof into a food or nutritional supplement.

In a method for preparing a food according to the invention, the food can first be prepared separately and then be combined with a sphingolipid in order to obtain a food according to the invention, with this sphingolipid being incorporated into the food. The food can be separately prepared in advance in known manners such as mixing, frying, deep-frying, cooking, steaming, roasting or poaching and can be cooled down, if necessary, before combining it with a sphingolipid in order to obtain a food according to the invention. According to another usable embodiment, during the preparation of the food, a sphingolipid is incorporated therein as a constituent.

To normal foods such as milk or soymeal, sphingolipids may also be added in order to obtain a food according to the invention. For this purpose, sphingolipids may, for instance, be purified from such foods and these purified sphingolipid preparations may be used for preparing a food according to the invention.

Transgenic crops or genetically modified organisms may also very suitably be used for increasing the natural content of sphingolipids in certain food crops or foods which are used in embodiments according to the invention or serve as sources for sphingolipid to be purified from them.

A method for the preparation of a medicine or pharmaceutical which can be used for improvement of the composition of the intestinal flora comprises, for instance, mixing the constituents and tabletting the mixture, optionally followed by coating the tablets thus obtained. The preparation of medicines which are dosed by means of alternative administration forms is known to a skilled person. On the basis of the present description, a skilled person is also able to formulate a method for the preparation of a nutritional supplement. Such a method will comprise, for instance, the steps of mixing the ingredients and dosing the composition thus obtained.

The amount of sphingolipid which is incorporated into a food according to the invention depends on the type of sphingolipid and on the use which is provided, and a skilled person will be able to determine this amount in the light of the present description.

A very suitable concentration in the intestine for improving the composition of the intestinal flora according to the present invention is a concentration of sphingolipid of 10-50 ppm. With such concentrations, a very effective and selective killing of specific species of bacteria can be achieved. The use according to the invention provides improvement of the intestinal flora, promotion of the intestinal health and control of intestinal infections.

Preferably, the use of the present application is directed to modifying bacterial populations by administering a sphingolipid as defined hereinabove, for instance as antibiotic in food or in medicaments to maintain or obtain a balance in the intestinal flora.

The invention will now be illustrated in and by the following examples, which are not to be understood as being limitative.

EXAMPLES

Example 1

Antimicrobial Activity of Sphingolipids

The antimicrobial activity of phytosphingosine, sphingomyelin, sphinganine acetate, sphingosine, glucosylceramide III and lysosphingomyelin was tested on agar plates, in liquid cultures, in the small intestine model TIM-I and in the large intestine model TIM-2 (EP 0 642 382 and U.S. Pat. No. 5,525,305).

The agar plates were prepared by dissolving or suspending the dry material in water and, after sterilization, pouring the agar out in Petri dishes according to standard procedures. The following media were used: Brain Heart Infusion Broth (BHI; Oxoid CM 225), Clostridium difficile Agar (DFA; Oxoid CM 601+SR 96), De Man-Rogosa-Sharpe Broth (MRS; Oxoid CM 359), De Man-Rogosa-SharpeAgar (MRSA; Oxoid CM 361), Plate Count Agar (PCA; Oxoid CM 325), Reinforced Clostridial Broth (RCB; Oxoid CM 149), Rogosa Agar (Oxoid CM 627), Trypton Soy Agar (TSA; Oxoid CM 131).

Reinforced Clostridial Blood Agar (RCBA) was prepared by suspending 52.5 g of Reinforced Clostridial Agar (RCA; Oxoid CM 151) and 5 g of glucose in 850 ml of demineralized water. The suspension was autoclaved for 15 min at 121° C. After cooling down to approximately 50° C., an amount of 75 ml of sterile horse blood (Oxoid SR 50) and 75 ml of a sterile 0.4% (w/v) China blue solution were added. The agar solution was poured into Petri dishes according to standard procedures.

In a first preliminary investigation, the sphingolipids were used to determine their antimicrobial activity on agar plates. For this purpose, TSA, MRSA and RCBA agar plates were spirally loaded with ethanol solutions of the sphingolipids in such a manner that the concentration as a function of the location on the plate changed from high on the outside of the plates to low in the center of the plates.

By applying liquid cultures of the bacteria, grown in BHI, MRS or RCB, having known cell densities (approx. $4 \times 10^8$ colony-forming units [CFU]) from the edge of the plate and streaking them towards the center of the plate (like spokes in a wheel), the "minimal inhibiting concentration" (MIC) could be determined on the basis of the location on the agar plate where no bacterial growth occurred anymore and the corresponding concentration of sphingolipid.

The following bacteria were grown in BHI and streaked on TSA plates: *Escherichia coli* 0157:H7, *Salmonella enteritidis*, *Listeria monocytogenes*, *Bacillus cereus*, *Streptococcus suis* type 2 and *Pseudomonas aeruginosa*.

The following lactic acid bacteria were grown in MRS and streaked on MRSA plates: *Leuconostoc carnosum*, *Lactobacillus sake*, *Lactobacillus acidophilus*, *Lactobacillus casei* and *Enterococcus hirae*.

The following anaerobic bacteria were grown in RCB and streaked on RCBA plates: *Bifidobacterium adolescentis*, *Bifidobacterium* spp., *Fusobacterium nucleatum*, *Clostridium perfringens*, *Clostridium* spp., *Clostridium difficile* and *Bacteroides fragilis*.

The PCA plates loaded with sphingolipids and bacteria were aerobically incubated for 48 hours at 30° C. and the MRSA and RCBA plates were incubated under anaerobic conditions for 72 hours at 30° C.

Table 1 shows the MIC values (in µg/ml) of the sphingolipids tested, for the aerobic and anaerobic bacteria. None of the Gram-negative bacteria (*E. coli* 0157:H7, *S. enteritidis* and *P. aeruginosa*) were inhibited by the sphingolipids. *L. monocytogenes, B. cereus, S. suis* type 2, *L. carnosum, B. adolescentis* and *C. difficile* were inhibited by all sphingolipids already at the lowest concentrations (0.3-6.4 µg/ml), except by sphingomyelin and glucosylceramide III, which do not inhibit any of the bacteria tested. The antimicrobial activity of the sphingolipids decreases from phytosphingosine>sphingosine>lysosphingomyelin=sphinganine.

TABLE 1

The MIC values (µg/ml) of sphingolipids for Gram-negative, Gram-positive and anaerobic Gram-positive bacteria.

| Bacterium | Phyto-sphingo-sine | Sphingo-sine | Lyso-sphingo-myelin | Sphinganine | Glucosyl-ceramide III | Sphingo-myelin | Control (ethanol) |
|---|---|---|---|---|---|---|---|
| *E. coli* O157:H7 | >731 | >731 | >365 | >731 | >365 | >731 | growth |
| *S. enteritidis* | >731 | >731 | >365 | >731 | >365 | >731 | growth |
| *P. aeruginosa* | >731 | >731 | >365 | >731 | >365 | >731 | growth |
| *L. monocytogenes* | 6.3 | <6.3 | <3.1 | <6.3 | >365 | >731 | growth |
| *S. suis* type 2 | 6.3 | <6.3 | <3.1 | <6.3 | >365 | >731 | growth |
| *B. cereus* | 6.3 | <6.3 | <3.1 | <6.3 | >365 | >731 | growth |
| *L. carnosum* | <0.3 | <6.3 | <3.1 | <0.3 | >365 | >731 | growth |
| *L. sake* | 2.2 | <6.3 | 20 | >70 | >365 | >731 | growth |
| *L. acidophilus* | >36.5 | <6.3 | 16.6 | 222 | >365 | >731 | growth |
| *L. casei* | >36.5 | <6.3 | >365 | 246 | >365 | >731 | growth |

TABLE 1-continued

The MIC values (µg/ml) of sphingolipids for Gram-negative,
Gram-positive and anaerobic Gram-positive bacteria.

| Bacterium | Phyto-sphingo-sine | Sphingo-sine | Lyso-sphingo-myelin | Sphinganine | Glucosyl-ceramide III | Sphingo-myelin | Control (ethanol) |
|---|---|---|---|---|---|---|---|
| E. hirae | >36.5 | 84 | >365 | >731 | >365 | >731 | growth |
| B. adolescentis | 8.0 | <6.3 | <3.1 | >73 | >365 | >731 | growth |
| Bif. spp. | 0.9 | <6.3 | 10 | 0.9 | >365 | >731 | growth |
| F. nucleatum | <6.3 | <6.3 | >365 | >731 | >365 | >731 | growth |
| B. fragilis | 2.1 | <6.3 | 11.4 | 0.3 | >365 | >731 | growth |
| C. perfringens | 5.9 | n.d. | n.d. | >36.5 | n.d. | n.d. | no growth |
| C. difficile | 5.7 | n.d. | n.d. | >73 | n.d. | n.d. | growth |
| C. spp. | 1.1 | <6.3 | <3.1 | >73 | >365 | >731 | growth |

Because, on agar plates, bacteria are exposed to the sphingolipids much longer than if they were present in the intestine, some antimicrobial tests were repeated in liquid media and the numbers of surviving anaerobic bacteria (*Lactobacillus acidophilis* and *Clostridium difficile*) as a function of the exposure time were determined.

For this purpose, the bacteria were first grown to a known cell density in separate media and subsequently diluted to 4.7 CFU/ml in ileum medium (25 g/l of D-glucose, 1.5 g/l of peptone (Oxoid L 41), 60 mmol/l of NaHCO3, 6 g/l of NaCl, 0.7 g/l of KH2PO4, 0.3 g/l of NaH2PO4, 0.15 g/l of egg lysozyme (Sigma L6876), 1.25 g/l of pancreatin (Sigma P1500), 0.75 g/l of agar and optionally pig bile extract (1.5 g/l; see experiments, Sigma B8631). A culture medium was chosen which simulates the contents of the ileum (end of the small intestine, just before the large intestine) with respect to the composition. The medium contained inter alia glucose, peptone, sodium bicarbonate, phosphate salts, egg lysozyme and pancreatin.

In special cases, also, a pig bile extract was added, although, normally, in the ileum, the bile has already been removed. During the experiments in the presence of phytosphingosine and sphinganine, after 1, 3 and 6 hours of incubation, the number of surviving microorganisms was determined by removing bacterial samples of equal volume from the medium and grafting them on separate plates. The number of anaerobically surviving colonies after 2 or 3 days at 37° C. was taken as a measure for the killing of the bacteria by the sphingolipids. FIG. 1 shows the development of the numbers of surviving colonies in time after addition of phytosphingosine or sphinganine (each at 2.5, 10 and 50 µg/ml).

It was found that bile is lethal to both bacteria and no extra bactericidal effect of the sphingolipids can be measured at concentrations to 50 µg/ml.

In the absence of bile in the ileum medium, within 200 minutes, *Lactobacillus acidophilus* and *Clostridium difficile* were virtually completely killed both by phytosphingosine and by sphinganine at concentrations of 10 and 50 µg/ml. Remarkably, without sphingolipids (controls), the number of surviving bacteria in the ileum medium also slowly decreases. Due to an unknown cause, sphinganine has a much higher MIC value for *Lactobacillus acidophilus* on agar plates (see Table 1) than in an anaerobic liquid medium.

Example 2

Intestinal Transport of Phytosphingosine and Sphinganine

Because the sphingolipids need to be transported together with the food to the small and large intestines to be able to be active there, the transport of phytosphingosine and sphinganine in the stomach and small intestine model TIM-1 was tested. Also, the transport of phytosphingosine in a fistulated pig was tested after the animal had been fed with feed containing phytosphingosine (1 wt. %). In a fistulated pig, the small intestine is uncoupled from the large intestine so that the digested feed at the end of the small intestine can be collected.

Both in the TIM-1 model and in the in vivo pig model, the sphingolipids were transported in amounts sufficient to be able to have an antimicrobial activity in the large intestine.

On agar plates, as described in Example 1, Gram-negative bacteria are insensitive to sphingolipids, but, in those conditions, Gram-positive bacteria are killed only by phytosphingosine, sphingosine, sphinganine and lysosphingomyelin. Depending on the sphingolipid and the bacterium, the typical effective doses are between 0.3 and 20 µg/ml. These concentrations are comparable to those used of current antibiotics. In liquid cultures, *Clostridium difficile* and *Lactobacillus acidophilus* are for the larger part killed within 200 minutes by phytosphingosine and sphinganine (at a concentration of 50 ppm). In the TIM-2 large intestine model, *Clostridium difficile* was killed a factor of 10 to 100 more rapidly than the other anaerobic bacteria present.

The addition of sphingolipids (to 1 wt. %) to the feed of rats had the result that the total cholesterol content in the blood plasma was reduced by 30% compared to the control group (Vesper et al. 1999. J. Nutr. 129, 1239-1250). A high cholesterol content is known to be one of the risk factors for atherosclerosis. No increase in weight due the addition of the extra sphingolipid to the feed could be measured.

It was found that a fistulated pig which received feed with 1 wt. % of phytosphingosine remained healthy and that the intestinal contents at the end of the small intestine contained sufficient phytosphingosine to be able to kill *Clostridium difficile* in the large intestine.

Example 3

Antimicrobial Activity and Transport of Phytosphingosine and Sphinganine in TIM-1

Antimicrobial Activity in TIM-1

Since phytosphingosine and sphinganine have a strong antimicrobial activity on plate and in liquid cultures, the experiments were repeated in the small intestine model TIM-1, using 20 µg/ml of sphingolipid in the presence of *Lactobacillus acidophilus* (on Rogosa agar plates) and *Clostridium difficile* (on *Clostridium difficile* agar). After plating the lumen samples on the respective agar plates, there appeared to be no demonstrable antimicrobial activity.

Probably due to the lumen composition (other lipids, proteins, protein fragments and cholic acids) or due to adsorption to the TIM-1 system itself (see below), the sphingolipids are freely available in concentrations too low to be antimicrobially active. But the sphingolipids are transported in the TIM-1 system to a sufficient extent (see below).

Transport

To investigate whether sphingolipids from the food are transported through the small intestine without being absorbed or being chemically or enzymatically modified in the small intestine, phytosphingosine and sphinganine were mixed in a standard Tim-1 food and exposed to a TIM-1 treatment. Of each sphingolipid, 5 mg per 100 grams of food (0.005 wt. %) in the food were tested. After starting the TIM-1 digestion processes in the TIM-1 stomach, at the fixed times, lumen samples of 100 grams were taken. Also, dialysate samples were taken from the material which was transported through the semi-permeable TIM-1 membrane. The dialysate samples varied between 1428 and 1122 grams. Table 2 shows sphingolipid concentrations in the different samples as they were determined by means of LC-MS. Next to the samples, the exposure time in minutes is given.

The TIM-1 membrane used was found to be impermeable to the sphingolipids while both sphingolipids were adequately transported through the system. A rough mass balance (sum of volume x concentrations) shows that only approx. 20% of the phytosphingosine and sphinganine used was found in the samples. A possible explanation may be that the sphingolipids adsorb to the plastic of the semi-permeable membranes and to the hoses of the TIM-1 model. This is a known phenomenon in TIM-1 studies with other hydrophobic substances such as carotenoids.

TABLE 2

Concentrations of sphingolipids in the different TIM-1 compartments during the TIM-1 digestion process

| TIM-1 sample | Phytosphingosine (µg/ml) | Sphinganine (µg/ml) |
|---|---|---|
| Food | 5.19 | 19.36 |
| Lumen jejunum 60' | 1.47 | 8.75 |
| Lumen jejunum 120' | 1.79 | 11.51 |
| Lumen jejunum 180' | 3.41 | 12.47 |
| Lumen jejunum 240' | 4.10 | 10.46 |
| Dialysate jejunum 0-120' | 0 | 0 |
| Dialysate jejunum 120-240' | 0 | 0 |
| Lumen ileum 60' | 0.20 | 0.74 |
| Lumen ileum 120' | 2.23 | 4.52 |
| Lumen ileum 180' | 2.22 | 5.30 |
| Lumen ileum 240' | 1.96 | 7.91 |
| Dialysate ileum 0-120' | 0 | 0 |
| Dialysate ileum 120-240' | 0 | 0 |
| Residue stomach/duodenum + dialysis fluid | 1.03 | 2.73 |
| Residue jejunum/ileum + dialysis fluid | 3.32 | 8.62 |

Example 4

Transport of Phytosphingosine in a Fistulated Pig

To investigate in an in vivo system whether sphingolipids from the food do actually arrive in the large intestine and are not prematurely absorbed or metabolized, pig basic feed to which phytosphingosine (1 wt. %) was added was fed to a fistulated pig.

The feed was prepared by mixing a solution of phytosphingosine in ethanol with the feed and drying it in vacuo. Every hour, the intestinal content (chymus) at the end of the small intestine was separately collected and frozen dry. The dry intestinal contents were then extracted with chloroform/methanol (2:1, v/v). The extracts were then filtered over glass wool and evaporated under a nitrogen flow. The residues were examined for the presence of phytosphingosine, sphingosine, sphinganine and sphingomyelin by means of LC-MS.

Figure 2:
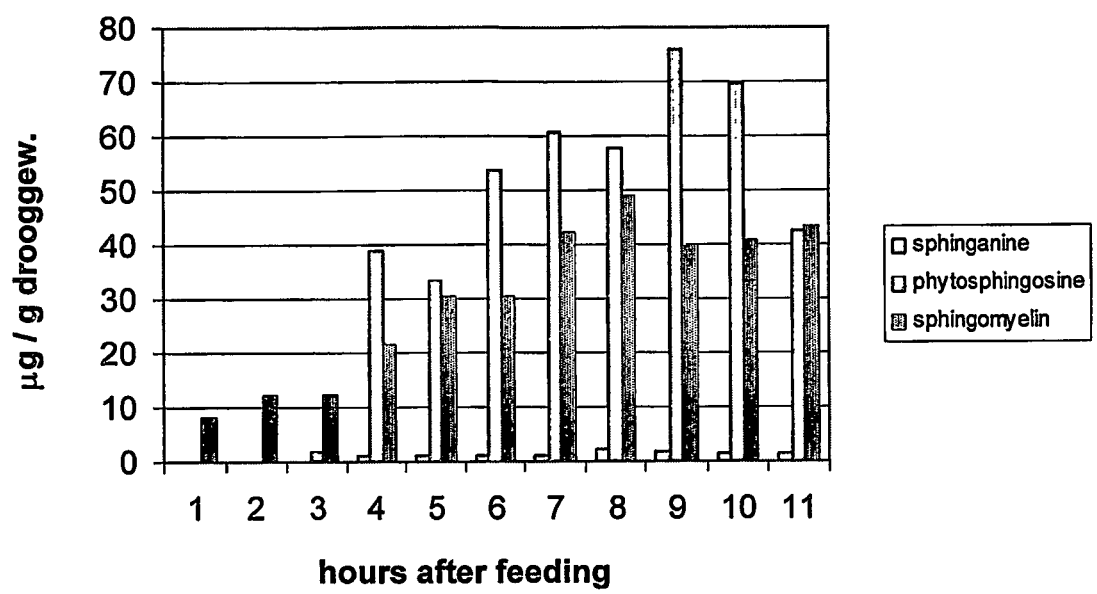
FIG. 2 shows the sphingolipid concentrations in the intestinal content of a fistulated pig collected at the end of the small intestine as a function of the time after feeding the pig with pig basic feed which contained 1 wt. % of phytosphingosine as described in Example 4.

FIG. 2 shows the amounts of the sphingolipids present in the intestinal contents in micrograms per gram of dry weight of the sample.

No sphingosine could be demonstrated in the intestinal contents. Phytosphingosine leaves the small intestine from two hours after feeding, with a maximum of 76 µg/g of dry intestinal contents after 9 hours.

Remarkably, in addition to phytosphingosine, also, small amounts of sphinganine and larger amounts of sphingomyelin are present in the intestinal contents at the end of the small intestine. These latter 2 sphingolipids are probably already naturally present in the food.

Example 5

Antimicrobial Activity of Phytosphingosine in TIM-2

*Clostridium difficile* is often found in the large intestine in humans and animals and causes diarrhea. To a standard TIM-2 food, a mixture of the following bacteria was added: *Bifidobacterium* (Log germ count 8.8), *Bacteroides* (Log germ count 9.7), sulfite-reducing *clostridia* (Log germ count 6.6), *Enterococcus* (Log germ count 8.7), *Lactobacillus* (Log germ count 8.5) and Enterobacteriaceae (Log germ count 6.6) (see starting values FIG. 3).

Figure 3:
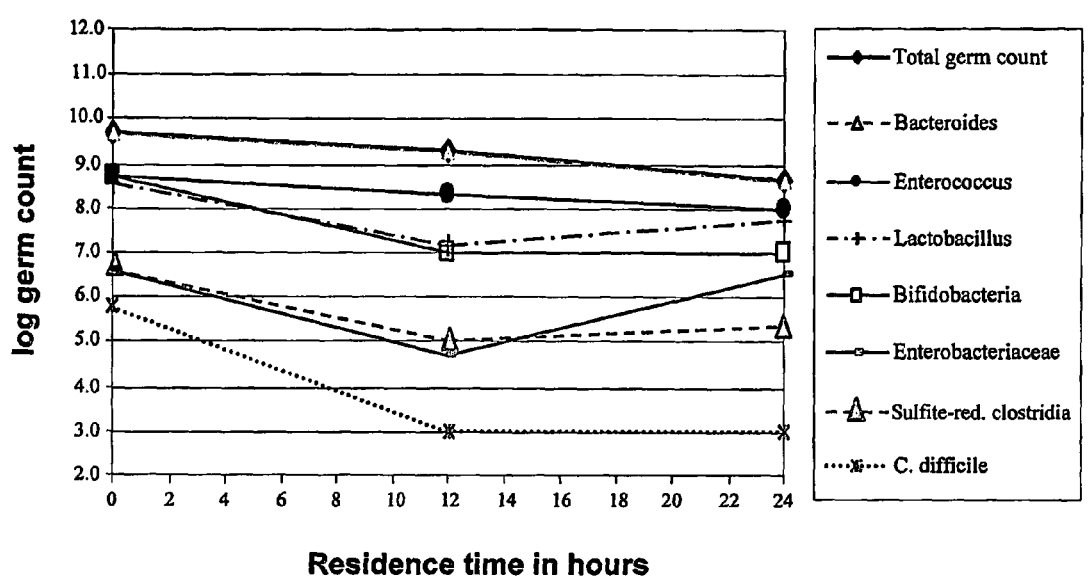
FIG. 3 shows the germ counts of the different anaerobic bacteria after incubation of the bacterial mixture in the TIM-2 large intestine model in the presence of 50 µg/ml of phytosphingosine as described in Example 5.

At point in time t=0, *Clostridium difficile* was added to an amount of approximately 5.75 log of CFU/ml. After mixing, phytosphingosine was introduced into the TIM-2 system in two concentrations (10 and 50 µg/ml). At points in time 0, 12, and 24 hours, samples were taken which were diluted and plated on agar plates selective for each bacterium (see above for the selective plates). The number of colonies of each bacterial strain was taken as a measure for the bacterial concentration in TIM-2. At 10 µg/ml of phytosphingosine, no significant killing of *C. difficile* or of other bacteria took place. At 50 µg/ml, a rapid and selective 550-fold decrease of *C. difficile* can be seen within 12 hours. The numbers of other bacteria decrease much less. *Bifidobacterium* decreases by a factor of 55, *Bacteroides* by a factor of 10, sulfite-reducing *Clostridium* by a factor of 36, *Enterococcus* by a factor of 5, *Lactobacillus* by a factor of 24 and the Enterobacteriaceae decrease by a factor of 77. FIG. 3 shows the logarithmic germ counts as a function of the exposure time. Germ counts lower than 3 log CFU/ml are, in practice, virtually always considered 0 because such low germ counts can no longer be properly determined.

CONCLUSION OF THE EXPERIMENTS

The results of the above-described tests show that, on agar plates, phytosphingosine, sphinganine, sphingosine and lysosphingomyelin have a strong antimicrobial activity against Gram-positive bacteria. Phytosphingosine and sphinganine also have a strong antimicrobial activity in liquid cultures. In the TIM-2 large intestine model, phytosphingosine has a selective antimicrobial activity against *Clostridium difficile*, which causes diarrhea. In the stomach/ small intestine model TIM-1, both sphinganine and phytosphingosine are transported to the large intestine to a sufficient extent to be able to be antimicrobially active there. Also in a pig, sufficient phytosphingosine from the feed was secreted at the end of the small intestine to be able to have the desired activity in the large intestine.

The invention claimed is:

1. A method for improving the composition of the intestinal flora of a bird or a mammal whose intestinal flora are out of balance, comprising
orally administering to a bird or a mammal in need thereof a food in which one or more sphingolipids chosen from the group consisting of phytosphingosine, sphingosine, lysosphingomyelin and sphinganine, or suitable salt thereof are overabundant, wherein the sphingolipid selectively kills or inhibits bacteria identified as being undesired for the proper functioning of the intestinal flora and leaves much less inhibited bacteria identified as being healthy to the intestinal flora to modify the composition of the intestinal flora in a desired direction.

2. A method according to claim 1, wherein said one or more sphingolipids are present in said food in an amount of 0.05 to 50 wt. %.

3. A method according to claim 1, wherein said sphingolipid is present in said food in an amount of 1 to 10 wt. %.

4. A method for improving the composition of the intestinal flora of a bird or a mammal whose intestinal flora is out of balance, comprising orally administering to a bird or a mammal in need thereof a pharmaceutical preparation comprising a sphingolipid chosen from the group consisting of phytosphingosine, sphingosine, lysosphingomyelin and sphinganine, or suitable salt thereof, and one or more excipients, wherein the sphingolipid selectively kills or inhibits bacteria identified as being undesired for the proper functioning of the intestinal flora without eliminating bacteria identified as being healthy to the intestinal flora.

5. A method according to any one of claims 1-4, wherein said sphingolipid is phytosphingosine.

6. The method according to claim 1, wherein said bird or mammal is suffering from one or more of diarrhea, an infection of the gastrointestinal tract, liver damage, intestinal cancer, poor immunological function, distension due to gas, poor digestion, poor absorption of nutrients, and vitamin deficiency.

7. The method according to claim 4, wherein said bird or mammal is suffering from one or more of diarrhea, an infection of the gastrointestinal tract, liver damage, intestinal cancer, poor immunological function, distension due to gas, poor digestion, poor absorption of nutrients, and vitamin deficiency.

* * * * *

UNITED STATES PATENT AND TRADEMARK OFFICE
CERTIFICATE OF CORRECTION

PATENT NO. : 8,703,172 B2
APPLICATION NO. : 10/542838
DATED : April 22, 2014
INVENTOR(S) : Willem Ferdinand Nieuwenhuizen Page 1 of 1

It is certified that error appears in the above-identified patent and that said Letters Patent is hereby corrected as shown below:

Title Page (73) Assignee:

"Nederlandse Organizatie voor
Toegepastnatuurwetenschappelijk
Onderzoek TNO, Delft (NL)"

Should read:

--Nederlandse Organisatie voor
toegepast-natuurwetenschappelijk
onderzoek TNO, Delft (NL)--

Signed and Sealed this
Eleventh Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,703,172 B2  Page 1 of 1
APPLICATION NO. : 10/542838
DATED : April 22, 2014
INVENTOR(S) : Willem Ferdinand Nieuwenhuizen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1744 days.

Signed and Sealed this
Twenty-ninth Day of September, 2015

Michelle K. Lee
*Director of the United States Patent and Trademark Office*